(12) United States Patent
Callahan

(10) Patent No.: US 9,689,819 B2
(45) Date of Patent: Jun. 27, 2017

(54) ELECTRONIC PSYCHROMETER AND/OR HUMIDISTAT WITH LOW TEMPERATURE AND HIGH HUMIDITY CAPABILITY

(71) Applicant: Christopher W Callahan, Cambridge, NY (US)

(72) Inventor: Christopher W Callahan, Cambridge, NY (US)

(73) Assignee: The University of Vermont and State Agricultural College, Burlington, VT (US)

(*) Notice: Subject to any disclaimer, the term of this patent is extended or adjusted under 35 U.S.C. 154(b) by 0 days.

(21) Appl. No.: 14/841,515

(22) Filed: Aug. 31, 2015

(65) Prior Publication Data

US 2016/0061757 A1    Mar. 3, 2016

Related U.S. Application Data

(60) Provisional application No. 62/043,746, filed on Aug. 29, 2014.

(51) Int. Cl.
*G01D 18/00* (2006.01)
*G01N 25/64* (2006.01)

(52) U.S. Cl.
CPC .................. *G01N 25/64* (2013.01)

(58) Field of Classification Search
CPC ........ G01P 21/00; G01N 25/64; G01N 25/62; G01N 33/246; G01K 15/00

USPC .................. 73/1.01, 77, 73, 338, 335; 374/1
See application file for complete search history.

(56) References Cited

U.S. PATENT DOCUMENTS

| 3,886,797 | A | * | 6/1975 | Bauer | G01N 25/64 73/29.02 |
| 4,559,823 | A | * | 12/1985 | Rosen | G01N 25/62 374/109 |
| 5,746,061 | A | * | 5/1998 | Kramer | B01D 53/265 374/39 |
| 6,038,922 | A | * | 3/2000 | Mauze | G01N 25/64 73/335.08 |
| 6,202,480 | B1 | * | 3/2001 | Mauze | G01N 25/64 374/109 |
| 2016/0061757 | A1 | * | 3/2016 | Callahan | G01N 25/64 62/176.1 |

* cited by examiner

*Primary Examiner* — Michael A Lyons
*Assistant Examiner* — Nigel Plumb

(57) ABSTRACT

The present invention has to do with a method and system for a high precision electronic psychrometer operable at low temperatures and high humidity environments. The electronic psychrometer includes thermistors for measuring wet and dry bulb temperatures and a wicked cage surrounding one of the thermistors. The wicking action of the wicked cage is controlled by an evaporation controller in conjunction with the wick's physical parameters. The electronic psychrometer determines relative humidity and provides a readout display and/or a control signal.

20 Claims, 2 Drawing Sheets

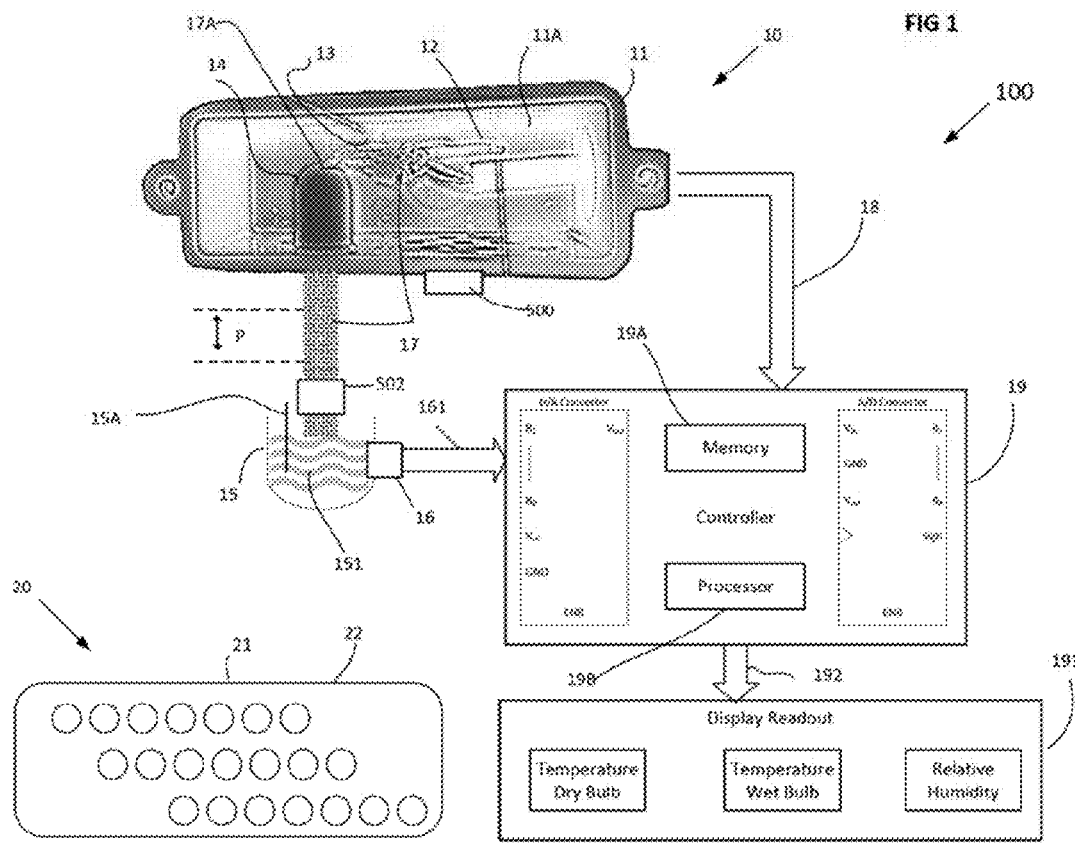
FIG 1
FIG 2
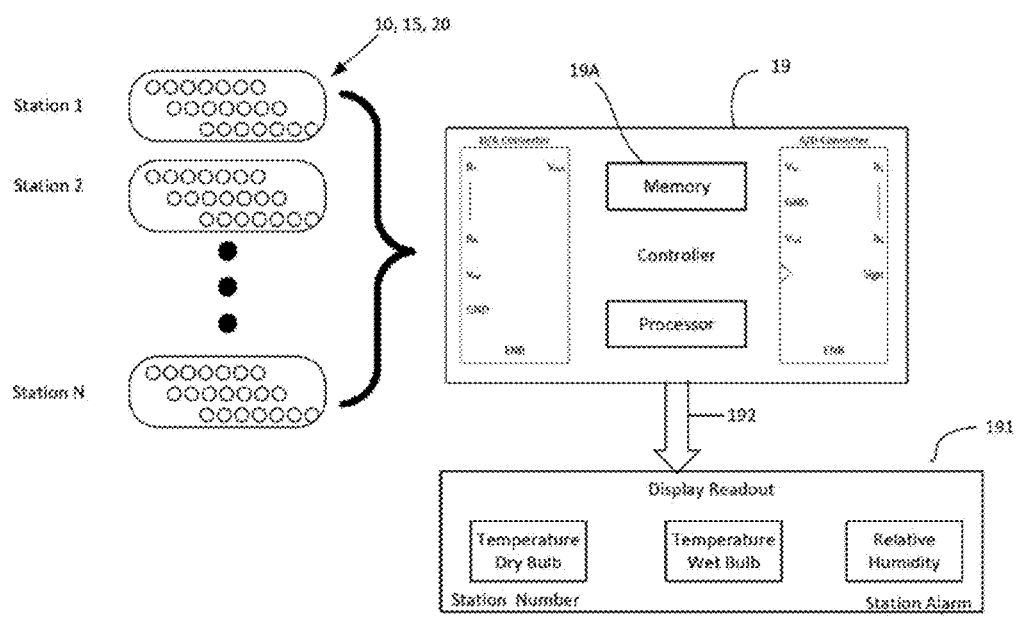
FIG 3

ELECTRONIC PSYCHROMETER AND/OR HUMIDISTAT WITH LOW TEMPERATURE AND HIGH HUMIDITY CAPABILITY

CROSS-REFERENCE TO RELATED APPLICATIONS

The present application is related to, claims the earliest available effective filing date(s) from (e.g., claims earliest available priority dates for other than provisional patent applications; claims benefits under 35 USC §119(e) for provisional patent applications), and incorporates by reference in its entirety all subject matter of the following listed application(s) (the "Related Applications") to the extent such subject matter is not inconsistent herewith; the present application also claims the earliest available effective filing date(s) from, and also incorporates by reference in its entirety all subject matter of any and all parent, grandparent, great-grandparent, etc. applications of the Related Application(s) to the extent such subject matter is not inconsistent herewith:

U.S. provisional patent application 62/043,746 entitled "Electronic Psychrometer and/or Humidistat with Low Temperature and High Humidity Capability", naming Christopher W. Callahan as inventor, filed 29 Aug. 2014.

BACKGROUND

1. Field of Use

This invention relates to an improved apparatus fir measuring relative humidity. More specifically, the invention relates to a high precision electronic. Psychrometer operable at low temperatures and high humidity environments.

2. Description of Prior Art (Background)

In general a psychrometer is an instrument consisting of two thermometers which are used in the measurement of the moisture content, or relative humidity (RH) of air or other gases. The bulb or sensing area of one of the thermometers either is covered by a thin piece of clean muslin cloth, or other wick material, wetted uniformly with distilled water or is otherwise coated with a film of distilled water. The temperatures of both the bulb and the air contacting the bulb are lowered by the evaporation which takes place when unsaturated air moves past the wetted bulb. An equilibrium temperature, termed the wet-bulb temperature will be reached; the equilibrium temperature closely approaches the lowest temperature to which air can be cooled by the evaporation of water into the unsaturated air. Moisture parameters, such as relative humidity and dew-point temperature, can be evaluated from the wet- and dry-bulb measurements by means of psychrometric tables and generally accepted closed form formulae for calculating water/air mixtures.

Relative Humidity (RH) is a measure of the degree to which air is saturated with water compared to the highest level of saturation at a given temperature. This is a ratio of the partial pressure (proportional content) of water in air at the actual conditions to the partial pressure of water in air at saturation (100% RH). Partial pressures of water in air are related to temperature.

The traditional method for determining RH is to use a manual sling Psychrometer which has two thermometers, one with a dry bulb and one with a wet bulb. The dry bulb thermometer is typical of thermometers in use in other applications and simply measures the air temperature. The wet bulb thermometer has a water saturated wick around it. When the thermometer is swung in the air to move air over the wet bulb, evaporation of water from this wick depresses the temperature of the bulb to a degree that corresponds to the saturation partial pressure of water in the air at the dry bulb temperature. Comparison of these two temperatures can provide an indirect measure of RH.

However, the long-term (6-12 month) storage of crops requires control of both storage temperature and humidity. Storage temperature is depressed to 32-40 degrees F. (crop dependent) in order to minimize the rate of respiration in the crops. Humidity is generally raised to 80-98% RH to reduce desiccation yet still avoid liquid water condensation on the crops. In recent field research pertaining to improved crop storage methods, it has been determined that there is a lack of suitable equipment for humidity measurement and control at low storage temperatures and high humidity.

The vast majority of humidity sensing equipment available is based on moisture absorbing, materials whose capacitance changes depending on the material moisture content. These sensors tend to have a precision of +/−2% RH from 20-80% RH at 70 degrees F., but then lose precision in the higher RH range and lower temperature range, straying, to +/−5% RH. It is this range that is most needed by those storing winter crops. Some sensors exist which demonstrate +/−2% RH precision up to 98% RH. But in all of these sensor types, excursions to 100% RH results in reduced precision and accuracy and can cause a mechanical failure or a need for recovery (heat and dry) in order to reuse the sensor. Additionally, these sensors may also suffer an unrecoverable electronic failure.

Thus, there is a technical challenge which exists in the measurement of high humidity in low temperature conditions; and, therefore control of equipment (e.g., humidifiers, dehumidifiers) based on these measurements.

BRIEF SUMMARY

The foregoing and other problems are overcome, and other advantages are realized, in accordance with the presently preferred embodiments of these teachings.

An electronic device for measurement of dry bulb and wet bulb space temperatures is disclosed. A microprocessor contains necessary software to calculate relative humidity from the dry and wet bulb space temperatures and to adjust an output as necessary to control humidity and/or temperature of the space.

The invention is also directed towards an electronic psychrometer having wet and dry temperature sensors, wherein the temperature sensors are substantially 10 k Ohm+/−0.05 deg. C. thermistors. The invention also includes a fan-less evaporator cage surrounding the thermistors, wherein the evaporator cage, or wick, comprises pick dimension P, wherein pick dimension P is the number of carrier crossings per longitudinal inch of the evaporator cage. Also included is a programmable controller and a computer readable medium, operatively coupled to the programmable controller. The computer readable medium contains a set of programmable controller instructions that, if executed by the programmable controller, are operable to: calibrate the wet and dry temperature sensors; and determine relative humidity with an accuracy of substantially +/−1% RH at 32 degrees F.

In accordance with one embodiment of the present invention an electronic psychrometer is provided. The electronic psychrometer includes a dry temperature sensor and a wet temperature sensor. An evaporator cage surrounds the at least one wet temperature sensor, wherein the evaporator cage comprises pick dimension P, wherein pick dimension P is the number of carrier crossings per longitudinal inch of the evaporator cage. Also include is a programmable controller and a computer readable medium, operatively coupled to the programmable controller. The computer readable medium contains a set of programmable controller instructions that, if executed by the programmable controller, are operable to determine relative humidity with an accuracy of substantially +/−1% RH at 32 degrees F.

The invention is also directed towards a method for calibrating an electronic psychrometer. The method includes providing a reference fluid having a known temperature. The method also includes providing wet and dry temperature sensors. The wet and dry temperature sensors are immersed or enveloped within the reference fluid and the temperatures reported by the sensors is compared to the known temperature of the reference fluid. A calibration temperature offset is determined from the difference between the reported temperatures and the known temperature.

BRIEF DESCRIPTION OF THE DRAWINGS

The subject matter which is regarded as the invention is particularly pointed out and distinctly claimed in the chums at the conclusion of the specification. The foregoing and other objects, features, and advantages of the invention are apparent from the following detailed description taken in conjunction with the accompanying drawings in which:

FIG. 1 is a pictorial illustration of an electronic psychrometer system in which the invention is implemented;

FIG. 2 is a pictorial illustration of a self-ventilating and adjustable ventilation cover plate in accordance with the invention shown in FIG. 1;

FIG. 3 is a pictorial illustration of a system of psychrometer systems in accordance with the invention shown in FIG. 1.

DETAILED DESCRIPTION

Figure 4:
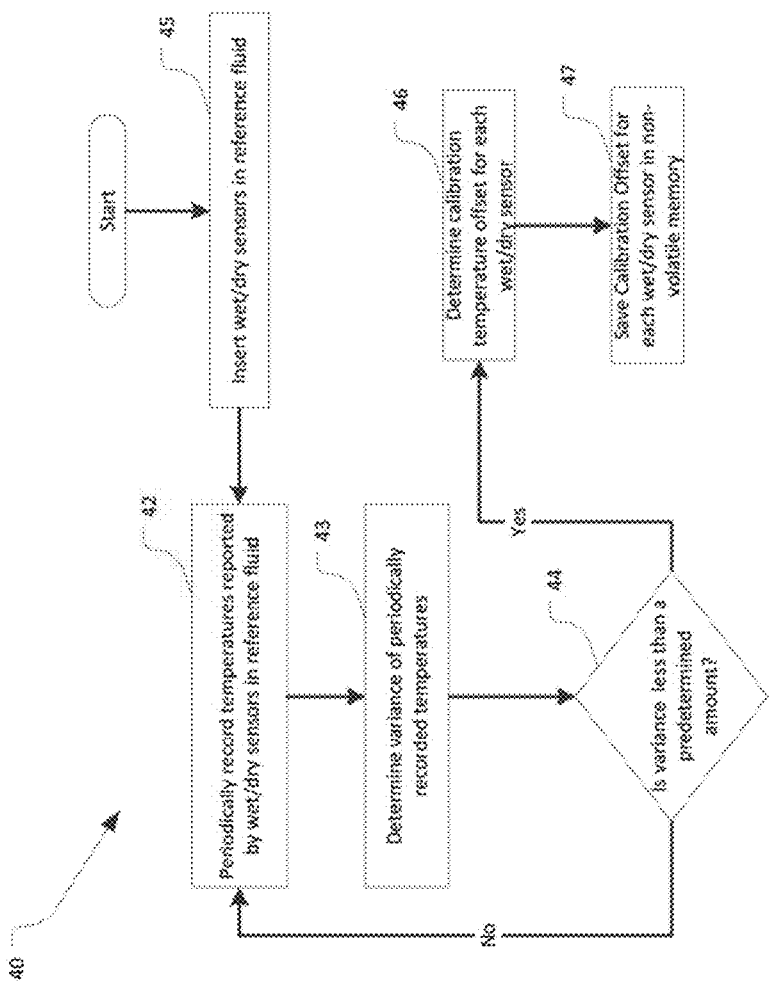
FIG. 4 is an illustration of one method for calibrating the wet/dry thermistors in accordance with the invention shown in FIG. 1.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example; and If the specification states a component or feature "may," "can," "could," "should," "preferably," "possibly," "typically," "optionally," "for example," or "might" (or other such language) be included or have a characteristic, that particular component or feature is not required to be included or to have the characteristic.

As noted earlier psychrometry is the principle whereby the measurement of a gas (often air) humidity is determined from simultaneous dry bulb thermometer and wet bulb thermometer measurements. The dry bulb thermometer measures the temperature of the gas. The temperature of the wet bulb thermometer depends on both the dry bulb temperature (e.g., ambient temperature) and humidity of the gas. The rate of evaporation of water from the wet bulb thermometer depends on the amount of water vapor present in the surrounding gas. The temperature of the wet bulb thermometer results from a balance between the evaporative cooling and convective heating by the ambient gas flows.

Wet-bulb and dry-bulb temperatures are digitally measured and relative humidity measurement proceeds by standard psychrometric equations. Water vapor pressure is estimated from the wet bulb and dry thermometer temperatures using the psychrometric equation, $$e = e_s(t_w) - \gamma(t_d - t_w) \qquad \text{eq. 1}$$

where e is the vapor pressure, $e_s(t_w)$ is the saturated vapor pressure at the wet bulb temperature ($t_w$), $t_d$ is dry bulb temperature, and $\gamma = 0.660$ (mb/° C.) when barometric pressure is 1000 mb.

Relative humidity is the ratio of actual water vapor present in gas to the maximum quantity which could saturate at the gas temperature. Thus, relative humidity (RH) is given by:

$$RH = 100 e/e_s(t_d) \qquad \text{eq. 2}$$

Referring now to FIG. 1, there is shown a diagram layout of an electronic psychrometer system 100 in which the invention is implemented. Included within the system 100 is remote temperature differentiator housing 11. Differentiator housing 11 includes wet bulb temperature sensor 13, dry bulb temperature sensor 12, wick 17, and evaporation controller 14. Also, shown in FIG. 1 is optional fan 500.

Still referring to FIG. 1, wet bulb temperature sensor 13 is a high accuracy negative temperature coefficient (NTC) thermistor (e.g., 10 kOhm+/−0.05 deg C.: US Sensor # PR103J2). It will be understood that temperature sensor 13 is referred to as a wet "bulb" temperature sensor and that the term bulb is common language stemming from sensors using liquid thermometers. Similar to web bulb temperature sensor 13, dry bulb temperature sensor 12 is also a high accuracy NTC thermistor. It will be appreciated that wet and dry bulb sensors 12, 13 may be substantially matched (electrical characteristics) NTC thermistors or offset (electrical characteristics) by a predetermined amount. In alternate embodiments the thermistors may be high accuracy positive temperature coefficient (PTC) thermistors, thermocouples (TC), or resistive thermal devices (RTD).

Still referring to FIG. 1, housing 11 may be any suitable shape or size to facilitate the balance between the evaporative cooling and convective heating by the ambient gas flows discussed earlier. It will be appreciated that in alternate embodiments the color of the housing 11 may be chosen to exploit air mixing by thermal or solar radiation. For example, the housing 11 may be colorized black to increase the internal ambient temperature and further facilitate the balanced discussed herein. Housing 11 may also be variably colorized to promote heating effects within one section of housing 11 and cooling effects in another section, thereby promoting convective air flow through the housing 11. Likewise, housing 11 may be a lighter color throughout to minimize solar heating by solar radiation. In alternate embodiments convective flow through housing 11 may be induced or facilitated by a heater resistor. It will be appreciated that the dimensions and characteristics (e.g., color) may be incorporated, and/or accounted for by controller 19 discussed herein.

Housing 11 also contains evaporation controller 14. Evaporation controller 14 exerts pressure on wick 17 at point 17A which controls the flow of moisture from reservoir 15, along wick 17, through evaporation controller 14 to be evaporated into the interior chamber 11A of housing 11. It will be appreciated that evaporation controller 14 works cooperatively with the characteristics of wick 17 to control the evaporation into the interior of housing 11. For example the pick dimension P, or Picks per inch—is the number of carrier crossing points per longitudinal inch of wick 17. Pick dimension P may be any suitable pick dimension, such as, for example, 2 carrier crossings per inch.

Still referring to FIG. 1, the water reserve 151 may be extended (e.g. less evaporation to the ambient air, by minimizing the length of wick 17 exposed to air. This can be done with placement of the reservoir 15 relative to the wick 17 and/or with a covering or sleeve 502 over the wick 17. For clarity only a partial covering 502 is shown.

Still referring to FIG. 1, reservoir container 15 may be any suitable container for holding liquid 151 (e.g. water). In alternate embodiments reservoir container 15 may also include sensor 16. Sensor 16 may communicate reservoir status to controller 19. For example status may include liquid level, temperature, or viscosity. Also shown in FIG. 1 is reservoir heater 15A. Reservoir heater may be any suitable heater such as for example, electric or solar and may be thermostatically controlled. Similarly reservoir 15 may be painted or otherwise colorized any suitable color for absorbing or reflecting sunlight or any other radiant light in order to adjust the temperature of the liquid 151 held in reservoir 15.

Also shown in FIG. 1 is controller 19. Controller 19 comprises: memory or computer readable medium 19B, at least one processor or programmable controller 19A, analog-to-digital and digital-to-analog converters necessary to process information relayed from sensors 12 and 13 via standard input/output channels or wireless connections; and, if present, from sensor 16. Controller 19 computes the relative humidity (RH) for display on display readout 191. It will be appreciated that RH may be computed by controller 19 according to equation 1 and equation 2 discussed earlier; or, any suitable algorithm for determining RH based upon wet and dry bulb temperatures. In alternate embodiments a secondary input of barometric pressure can be included to more accurately calculate saturation, however in mathematical modeling the impact of pressure is generally negligible in RH calculation.

FIG. 1 also shows connectors 18 and 161 for transmitting sensor data from housing 11 and container 15, respectively. It will be appreciated that connectors 18 and/or 161 may be any suitable connector including wireless.

Referring also to FIG. 2 there is shown a pictorial illustration of a self-ventilating and adjustable ventilation cover plate 20 in accordance with the invention shown in FIG. 1. Ventilation cover plate 20 includes cover 21 and ventilation cavities 22. Cover plate 21 is suitably sized and shaped to enclosed housing 11 interior chamber 11A. Ventilation cavities 22 may be any suitable size, number, and shape to cooperatively work with evaporation controller 14 and wick 17 to control the evaporation of liquid 151 into the interior chamber 11A of housing 11.

Referring also to FIG. 3 there is shown a pictorial illustration of a system of psychrometer systems in accordance with the invention shown in FIG. 1. It will be understood that any suitable number of enclosed psychrometers 10 may be distributed in a space. Each of the psychrometers is suitably connected to controller 19 via a suitable connector, e.g., wire or wireless. Controller 19 monitors and determines the RH value for each station and displays on display 191. It will also be understood that controller 19 includes the logic and circuitry necessary to display warnings and or alarms if the RH for any given station is not within a specified range; or, if the liquid at each station is below a predetermined level. Alarms may be any suitable combination of visual or audio alarms. In addition, alarms may be communicated over an internet or cellular connection. It will be appreciated that any suitable configuration may be employed. For example, a configuration where each sensor has the required controller 19 to conduct the RH calculation and sends data, via a wireless connection or hardline, to a main controller which handles output controls. The alarm signal may also include the logic and resources necessary to drive humidifiers and/or dehumidifiers (400) to bring relative humidity to non-alarm levels.

Referring also to FIG. 4 there is shown an illustration of one method 40 for calibrating the wet/dry thermistors in accordance with the invention shown in FIG. 1. It will be appreciated that synchronous calibration of the wet-bulb and dry-bulb temperature sensors is critical to accuracy. The first step 45 immerses the wet/dry sensors in reference fluid with a known temperature, such as for example, a stirred ice bath at 0 C (32 F). It will be appreciated that any suitable reference fluid may be used, such as, for example, a 100 degree C. boiling bath for applications requiring high temperature accuracy. The processor (FIG. 1-19B) monitors the temperatures reported by the wet/dry sensors periodically, e.g., every second 42 for ten seconds, for example. If the variance of the array of temperature readings is less than a predetermined amount 44 the processor 19B determines 46 the calibration temperature offset (from the reference fluid temperature) for each wet/dry sensor. The processor 19B saves the calibration offset for each wet/dry sensor in non-volatile memory 19A. Otherwise, if the variance is greater than the predetermined amount another array of temperature values is measured 42. It will be appreciated that calibration of the temperature sensors as described overcomes two prior art problems. First, manufacturer tolerance on temperature vs. resistance for thermistors (or other sensors) is generally rated at 20 or 25 C, not 0 C resulting in drift in the desired measurement regime. In addition, there is often integration resistance deviation when attaching the sensors or when using wire for remote placement of the sensors.

Prototype Description

A prototype utilized two NTC 10 k Ohm thermistors in a voltage dividing circuit with a fixed 10 k Ohm resistor. With reasonable calibration (see FIG. 4), the temperature of a thermistor changes its resistance in a predictably precise and accurate manner. Using the voltage dividing circuit, this resistance is indirectly measured by the voltage across the fixed resistor. An Arduino Uno microcontroller supplied 5 VDC +/− voltage to the voltage dividers and measured the circuit voltage using a 10-bit analog to digital converter. In this prototype the Arduino Uno microcontroller software assumed 5 VDC for calculating resistance of the thermistors, however an alternate embodiment measures the bus voltage and incorporates this into the calculation to reduce error. One of the thermistors is referenced to air directly to measure dry bulb temperature. The other is wrapped in a wick used for manual sling psychrometers with the far end of the wick placed in a reservoir of water to saturate the wick remotely. This sensor measures wet bulb temperatures. In prototype experiments it was expected that air flow over the wet bulb thermistor would be required, similar to the need for swinging a manual psychrometer. However, it was noted in the first experiment that this was not needed since the thermal mass of the thermistor is considerably less than that of a traditional liquid thermometer and its fluid in the manual sling psychrometer; and, thus requires lower heat transfer rates to reach equilibrium at the wet bulb temperature. The coarseness and other characteristics of the wick are also important in this design element; the wick used initially was quite open and loose allowing for good evaporation and air flow dose to the measurement surface. Regardless, the behavior was repeated and is predictable.

Initial Results

FIRST PROTOTYPE—Using high precision thermistors a prototype circuit and associated software was developed to measure dry bulb and wet bulb temperatures. The prototype thermistors are mounted on a breadboard, but would eventually be mounted remotely from the main circuit, connected with wire or wireless connections. Thermistors can be made to be moisture resistant with potting (epoxy) and can also be manufactured to very high precision (+/−0.1 deg. F.). The measurement approach used in this design should result in a more rugged, precise, and accurate measurement of RH in low temperature high humidity environments at a material cost under $50.

SECOND PROTOTYPE (See FIG. 1)—A remote housing 11 having two openings was provided. A rubber stopper was used to plug one of the conduit holes and to allow CAT5e cabling to enter the housing. The evaporation controller 14 was glued into the other opening allowing the connection of the water reservoir 15 and a controlled, wick water supply 151 with minimal evaporation from the bottle. Various size bottles can be used, this prototype used a 1 fl oz size.

High accuracy NTC thermistors were used in the second prototype (10 kOhm+/−0.05 deg. C. US Sensor #PR103J2). No other significant changes were made to the circuit in this build. In initial tests of this build, it was found that an optional air flow over the wet-bulb thermistor could be used to stably depress the wet-bulb temperature. A small fan (Orion # OD2510-05HB) was integrated with desired results. The fan can be powered by any suitable means, e.g., battery power, solar powered, etc.

Conclusions

The prototypes used standard 10 k Ohm fixed resistors in the voltage divider. The actual resistance of the resistors was measured and used in the software-based calculation, but higher precision resistors would provide a more accurate RH calculation. Matching of the fixed resistors to the expected resistance of the thermistors in the measurement range results in maximum precision of the instrument.

The prototype or proof of concept used a laptop computer and USB connection for power and logging of results. A local LCD screen and power source were integrated into the prototype design. Other options for reporting sensor data are available for uploading data to cloud based data programs (Mojyle, etc.), email via Ethernet, or direct SMS text message communication via cell.

The prototype uses an Arduino Uno 10 bit analog to digital convertor which results in an output precision of about 0.09%. It will be appreciated that higher bit convertors would result in higher precision.

Referring to the figures it will be appreciated that item 400 (FIG. 3) represents a controlled device, such as, for example, a humidifier, a dehumidifier, a fan, or the like. It will be understood that devices such as the aforementioned may be controlled by controller 19 according to the calculated RH levels. There are currently no low temperature, high humidity humidistats on the market that are suitable for these applications. The microcontroller 19 may be programmed to provide control of such a system resulting in a very precise and stable control system for RH in storage.

It should be understood that the foregoing description is only illustrative of the invention. Thus, various alternatives and modifications can be devised by those skilled in the art without departing from the invention.

For example, enclosure of the sensing probes with careful attention to aspiration helps to avoid erratic readings during a compressor cycle in the refrigeration system. When the compressor runs, the air coming off an evaporator in a cooler will be very cold and very dry which may drive the dry bulb temperature lower very quickly. The wet-bulb is enclosed in a moistened wick and takes longer to respond. This results in an RH inversion which sends it above 100% (not possible). In an alternate embodiment a piece of dry wick material, same material as the wet-bulb, may be used to cover the dry bulb to make their dynamic thermal response relatively more equal. The other is using the enclosure lid. Alternatively, software processing by processor 19B may identify the situation and disregard the data and/or annotate the data stream to clarify it.

Accordingly, the present invention is intended to embrace all such alternatives, modifications and variances that fall within the scope a the appended claims.

What is claimed is:

1. An electronic psychrometer comprising:
   a dry temperature sensor;
   a wet temperature sensor;
   a fan-less evaporator cage surrounding the at least one wet temperature sensor, wherein the evaporator cage comprises pick dimension P, wherein pick dimension P is the number of carrier crossings per longitudinal inch of the evaporator cage;
   a programmable controller;
   a computer readable medium, operatively coupled to the programmable controller, wherein the computer readable medium contains:
      a set of programmable controller instructions that, if executed by the programmable controller, are operable to determine relative humidity (RH) with an accuracy of substantially +/−1% RH.

2. The electronic psychrometer as in claim 1 wherein the dry temperature sensor comprises a substantially 10 k Ohm+/−0.05 deg. C. thermistor.

3. The electronic psychrometer as in claim 1 wherein the wet temperature sensor comprises a substantially 10 k Ohm+/−0.05 deg. C. thermistor.

4. The electronic psychrometer as in claim 1 wherein the computer readable medium contains:
   a set of programmable controller instructions that, if executed by the programmable controller, are operable to determine the operational offset of the wet and dry temperature sensors from 0 C (32 F).

5. The electronic psychrometer as in claim 1 further comprising:
   a reservoir for holding a water reserve;
   a wick for providing fluidic communication between the reservoir and the evaporator cage.

6. The electronic psychrometer as in claim 5 further comprising a reservoir heater for heating the water reserve.

7. The electronic psychrometer as in claim 6 wherein the reservoir heater comprises an electric reservoir heater.

8. The electronic psychrometer as in claim 6 wherein the reservoir heater comprises a solar reservoir heater.

9. The electronic psychrometer as in claim 5 further comprising a wick cover.

10. The electronic psychrometer as in claim 1 further comprising a display for displaying:
    dry bulb temperature;
    wet bulb temperature; and
    relative humidity with an accuracy of substantially +/−1% RH.

11. The electronic psychrometer as in claim 10 wherein the display further comprises an alarm signal.

12. The electronic psychrometer as in claim 11 wherein the alarm signal comprises the logic and resources necessary to drive humidifiers and/or dehumidifiers to bring relative humidity to non-alarm levels.

13. The electronic psychrometer as in claim 1 wherein the dry temperature sensor comprises a second evaporator cage not in fluidic communication with the reservoir.

14. A method for calibrating an electronic psychrometer, wherein the method comprises: providing a reference fluid having a known temperature; providing at least one wet sensor; providing at least one dry sensor: providing a fan-less evaporator cage surrounding the at least one wet temperature sensor, wherein the evaporator cage comprises pick dimension P, wherein pick dimension P is the number of carrier crossings per longitudinal inch of the evaporator cage; enveloping the at least one wet sensor and the at least one dry sensor within the reference fluid; measuring the temperatures reported by the at least one wet sensor and the at least one dry sensor; providing a programmable controller for determining a calibration temperature offset between the temperatures reported by the at least one wet sensor and the at least one dry sensor and the known temperature, wherein the determining calibration accuracy is substantially within +−; 1%.

15. The method as in claim 14 wherein, measuring the measuring the temperatures reported by the at least one wet sensor and the at least one dry sensor (wet/dry sensor) further comprises:
    determining an array of temperature values;
    computing a variance associated with the array of temperature values; and
    determining if the variance is less than a predetermined amount.

16. The method as in claim 14 wherein providing the reference fluid having a known temperature further comprises providing a reference fluid at 0 degrees Celsius.

17. A psychrometer comprising: a dry temperature sensor, wherein the dry temperature sensor comprises a substantially 10 k Ohm+/−0.05 deg. C. thermistor; a wet temperature sensor, wherein the wet temperature sensor comprises a substantially 1 Ok Ohm+/0.05 deg. C. thermistor; a reservoir for holding a fluid reserve; an evaporator cage surrounding the at least one wet temperature sensor, wherein the evaporator cage comprises pick dimension P, wherein pick dimension P is the number of carrier crossings per longitudinal inch of the evaporator cage; a wick for providing fluidic communication between the fluid reserve and the evaporator cage; a programmable controller; and a computer readable medium, operatively coupled to the programmable controller, wherein the computer readable medium contains: a set of programmable controller instructions that, if executed by the programmable controller, are operable to determine relative humidity, with an accuracy of substantially +−; 1% RH, a set of programmable controller instructions that, if executed by the programmable controller, are operable to determine the operational offset of the wet and dry temperature sensors from 0 C (32 F).

18. The psychrometer as in claim 17 further comprising a reservoir heater for heating the water reserve.

19. The psychrometer as in claim 17 wherein the wick further comprises a wick cover.

20. The psychrometer as in claim 17 further comprising device controlling outputs for lowering or raising relative humidity in response to the determined relative humidity.

* * * * *